United States Patent
Andersson

(10) Patent No.: US 10,206,820 B2
(45) Date of Patent: *Feb. 19, 2019

(54) EPIDERMAL DOWN-GROWTH BARRIER

(71) Applicant: Cochlear Limited, Macquarie University, NSW OT (AU)

(72) Inventor: Marcus Andersson, Gothenburg (SE)

(73) Assignee: Cochlear Limited, Macquarie University, NSW (AU)

(*) Notice: Subject to any disclaimer, the term of this patent is extended or adjusted under 35 U.S.C. 154(b) by 0 days.

This patent is subject to a terminal disclaimer.

(21) Appl. No.: 15/477,571

(22) Filed: Apr. 3, 2017

(65) Prior Publication Data

US 2017/0202709 A1   Jul. 20, 2017

Related U.S. Application Data

(63) Continuation of application No. 13/578,004, filed as application No. PCT/US2011/024373 on Feb. 10, 2011, now Pat. No. 9,610,433.

(30) Foreign Application Priority Data

Feb. 10, 2010 (AU) .................... 2010200485

(51) Int. Cl.
*A61B 17/86* (2006.01)
*H04R 25/00* (2006.01)
(Continued)

(52) U.S. Cl.
CPC ......... *A61F 11/00* (2013.01); *A61M 39/0247* (2013.01); *H04R 25/606* (2013.01);
(Continued)

(58) Field of Classification Search
CPC ....... A61M 2039/0261; A61M 39/0247; A61F 11/00; A61F 11/008; H04R 25/606
See application file for complete search history.

(56) References Cited

U.S. PATENT DOCUMENTS 4,488,877 A  12/1984 Klein et al.
4,578,063 A   3/1986 Inman et al.
(Continued)

FOREIGN PATENT DOCUMENTS

EP   0367354 A1   5/1990
WO  2008062173 A1   5/2008
WO  2008143574 A1  11/2008

OTHER PUBLICATIONS

George D. Winter, "Transcutaneous Implants: Reactions of the Skin-Implant Interface," J. Biomed. Mater. Res. Symposium, No. 5 (Part 1), pp. 99-113 (1974).
(Continued)

*Primary Examiner* — Thaddeus B Cox
(74) *Attorney, Agent, or Firm* — Pilloff & Passino LLP; Martin J. Cosenza

(57) ABSTRACT

A percutaneous implant for reducing the risk of post-implant infection by reducing the likelihood of epidermal down-growth between the dermis of the skin and the implant. In one example, the implant comprises a barrier member between the epidermis and the dermis about the implant. In another example, a barrier is provided by removing a portion of the epidermis from the dermis about the implant.

33 Claims, 15 Drawing Sheets

(51) Int. Cl.
*A61F 11/00* (2006.01)
*A61M 39/02* (2006.01)

(52) U.S. Cl.
CPC ......... *A61B 17/8605* (2013.01); *A61F 11/008* (2013.01); *A61M 2039/0261* (2013.01); *H04R 2460/13* (2013.01)

(56) References Cited

U.S. PATENT DOCUMENTS

| | | |
|---|---|---|
| 4,634,422 A | 1/1987 | Kantrowitz et al. |
| 4,781,176 A | 11/1988 | Ravo |
| 4,886,502 A | 12/1989 | Poirier et al. |
| 4,897,081 A | 1/1990 | Poirier et al. |
| 5,833,641 A | 11/1998 | Curtis et al. |
| 5,954,506 A | 9/1999 | Tanaka |
| 8,554,329 B1 | 10/2013 | Mann et al. |
| 2001/0032022 A1 | 10/2001 | Ricci et al. |
| 2004/0204686 A1 | 10/2004 | Porter et al. |
| 2006/0041318 A1 | 2/2006 | Shannon |
| 2007/0060891 A1 | 3/2007 | Skiera et al. |
| 2007/0083078 A1 | 4/2007 | Easter et al. |
| 2007/0149949 A1 | 6/2007 | Porter et al. |
| 2007/0218102 A1 | 9/2007 | Chudzik et al. |
| 2008/0243216 A1* | 10/2008 | Zilberman ........... A61N 1/0558 607/116 |
| 2009/0082817 A1 | 3/2009 | Jinton et al. |
| 2009/0187233 A1 | 7/2009 | Stracener |
| 2009/0247810 A1 | 10/2009 | Parker et al. |
| 2013/0041206 A1 | 2/2013 | Andersson |

OTHER PUBLICATIONS

International Search Report, Application No. PCT/US2011/024373, dated May 17, 2011.
Extended European Search Report for Application No. 11742806.0, dated Dec. 3, 2013.

* cited by examiner

EPIDERMAL DOWN-GROWTH BARRIER

CROSS-REFERENCE TO RELATED APPLICATIONS

The present application is a Continuation Application of U.S. patent application Ser. No. 13/578,004, filed Oct. 31, 2012, now U.S. Pat. No. 9,610,433, naming Marcus Andersson as an inventor, which is a National Stage of PCT/US11/24373, filed Feb. 10, 2011, which claims priority to Australia Application No. 2010200485, filed Feb. 10, 2010. The entire contents of these applications are incorporated herein by reference in their entirety.

BACKGROUND

Field of Invention

The present invention relates to percutaneous implants, and more particularly, to an epidermal down-growth barrier.

Related Art

Percutaneous implants are devices that extend through the skin and are used in a wide variety of applications. Percutaneous devices include, but are not limited to, catheters, tracheotomy devices, and orthopaedic pins or anchors for external fixation devices. In certain circumstances, the percutaneous devices are bone-anchored implants used, for example, with a bone conduction hearing device comprising an external unit which transforms received sound into mechanical vibrations. The mechanical vibrations are conducted to a hearing impaired recipient's skull via a bone-anchored implant comprising an abutment attached to a bone fixture implanted in the skull. The vibrations are then transmitted mechanically via the skull bone directly to the recipient's inner ear, thereby generating movement of the inner fluid and perception of sound by the recipient. One such exemplary bone conduct hearing device is the Baha® hearing implant system marketed by Cochlear Bone Anchored Solutions AB in Molnlyeke, Sweden.

As noted above, bone-anchored implants are generally used with bone conduction devices comprises a bone fixture or anchoring element in the form of an implanted titanium screw installed in the bone behind the recipient's ear. In some anchoring arrangements, the skin is penetrated, which makes the vibratory transmission very efficient.

SUMMARY

In accordance with one embodiment of the present invention, a percutaneous implant is provided. The implant comprises a body portion extending through the skin of a recipient, the skin having an epidermis and a dermis; and a barrier member positioned around the body portion to substantially separate the dermis from the epidermis at the surface of the body of the implant when the percutaneous implant is implanted.

In accordance with another embodiment of the present invention, a method of implanting a percutaneous implant in a recipient is provided. The method comprises: creating an incision in the recipient's skin, including the epidermis, dermis and other tissue; positioning the percutaneous implant through the incision; positioning the dermis and other tissue adjacent the implant; providing a barrier between the epidermis and dermis adjacent to the implant; and positioning the epidermis to be separated from the dermis by the barrier.

BRIEF DESCRIPTION OF THE DRAWINGS

The various aspects of the present invention will now be described in detail with reference to the following drawings in which.

DETAILED DESCRIPTION

Embodiments of the present invention are generally directed to a barrier for preventing epidermal down-growth adjacent a percutaneous implant. In certain embodiments, the barrier comprises a member disposed around the body of the percutaneous implant between the patient's epidermis and dermis. In such embodiments, the separation of the epidermis from the dermis by the barrier member prevents the epidermis from growing between the dermis and the implant, thereby allowing the dermis to attach to the implant. In certain aspects of the present invention, the barrier member comprises a substantially planar member circumferentially extending from the surface of the implant. The barrier member has a thickness and a circumferential width between the implant surface and outer edge of the barrier member.

In other embodiments, the percutaneous implant is implanted in the patient using a method that prevents epidermal down-growth. More specifically, in these embodiments a section of the epidermis around the implant is removed during implantation of the percutaneous implant. The removed section of epidermis has a width such that the epidermis will not grow back to reach the surface of the implant until after the dermis is sufficiently attached to the implant.

Embodiments of the present invention will be primarily described with reference to percutaneous implants in the form of bone-anchored implants usable with bone conduction hearing aid devices. However, it would be appreciated that various aspects of the present invention may be used in relation to any bone-anchored or non-bone-anchored percutaneous implant, including catheters, tracheotomy devices, and orthopaedic external fixation devices. As used herein, a perctunaeous implant is any implant that extends through the skin of a recipient, whether or not the implant is fixed to another part of the body, and whether or not there is any fixture element, or other features such as a base. In one example, embodiments of the present invention may be used in connection with facial prostheses such as Vistafix™, marketed by Cochlear Limited, Australia.

Figure 1:
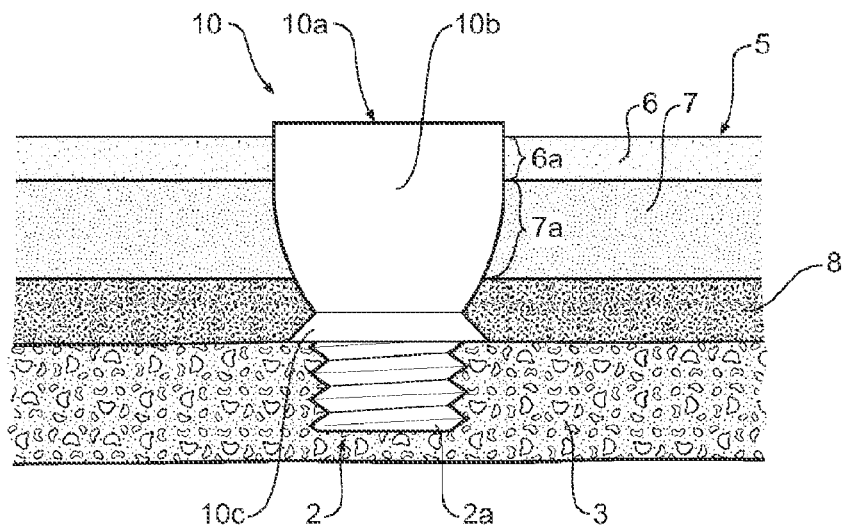
FIG. 1 illustrates a conventional percutaneous bone-anchored implant.

FIG. 1 shows a conventional bone-anchored implant 10 configured for attachment to an external device such as a bone conduction hearing aid (not shown). Implant 10 is shown in implanted in a recipient having a bone 3, skin 5 and other tissue 8 disposed between the skin and the bone. As is well known, skin 5 comprises an outermost layer known as epidermis 6, and a layer below the epidermis known as dermis 7.

As shown, implant 10 comprises a body including a fixture element 2 anchored to bone 3 via screw threads 21. In this arrangement, the body of implant 10 also comprises an abutment 10a having a main portion 10b and, in this exemplary arrangement, a base 10c. Base 10c may extend outwards and provide a stopping surface to prevent implant 10 from being inserted too deeply into bone 3. Additionally, abutment 10a extends through skin 5 to provide an accessible portion above the skin. This accessible portion provides a element to which a bone conduction hearing aid or other external device may be connected.

The interface between implant 10 and the various layers of the skin 5 are shown as implant-epidermis interface 6a, and implant-dermis interface 7a. Once the implant system 10 has been implanted, over time, skin 5 heals around the wound and bonds to the surface of the implant system.

A problem with percutaneous implant devices is the risk of infections and inflammation at the skin-implant interfaces 6a and 7a. The infections are a result of bacterial colonization occurring at the area around the interface. One major cause of infections results from epidermal down-growth that occurs when epidermis 6 grows down between dermis and implant 10 at the implant-dermis interface 7a. This down-growth forms a sinus tract (or pocket) between dermis 7 and implant 10 in which bacteria may grow, thereby resulting in an increased risk of infection that may then require implant explantation. One reason for the sinus formation is likely to be due to the inherent wound healing action of epidermis 6 to cover the dermis, Specifically, the main purpose of the epidermis is to seal of the wound (replacing the temporary blood clot/scab seal) from outside agents such as bacteria, particles and toxic elements. Within hours after a percutaneous implantation, the epidermal cell layers are starting to cover the dermal tissue. Only if the dermis (and sub dermal tissue) is firmly attached to the implant, the epidermal down-growth will stop.

Furthermore, dermis 7 does not attach quickly to some metals commonly used for medical implants, such as titanium, thereby allowing epidermis 6 to penetrate between implant 10 and the dermis. Furthermore, the growing of epidermis 6 between dermis 7 and implant 10 increases the likelihood that dermis 7 will not be able to properly attach to implant 10. This provides further opportunity for infection, as well as impeding the interface resistance to shear stress.

The above problems can be persistent and cause infections. The bacteria can invade the implant-tissue area directly at the implant-skin-air junction. Cleaning of the interface is of course very important to keep the area free from problems, however, even regular cleaning and disinfection is not always entirely successful.

To reduce the likelihood of infection, in convention surgical procedures a large amount of soft tissue is removed around the implant. Specifically, subcutaneous tissue is removed around the implant to thin the skin down to a minimum, thereby ensuring that the pockets formed as a result of epidermal down-growth are smaller. However, thinning the skin dorm to a minimum has drawbacks, including the large amount of surgical time required, the added complications for re-growth of skin that leads to increased susceptibility of infection and sometimes it leads to overgrowth due to scarring behavior of the tissue, the skin reduction leaves a permanent hairless divot which is unappealing to people. Additionally, thinning down the soft tissue also leaves it more vulnerable and skin necrosis sometimes occurs In addition, the soil tissue reduction removes the nerves in that area leaving a sensation of numbness. Accordingly, the soft tissue reduction is thus a trade off in order to reach a long lasting skin penetration and is an impediment to certain recipients receiving a percutaneous implant.

Figure 2:
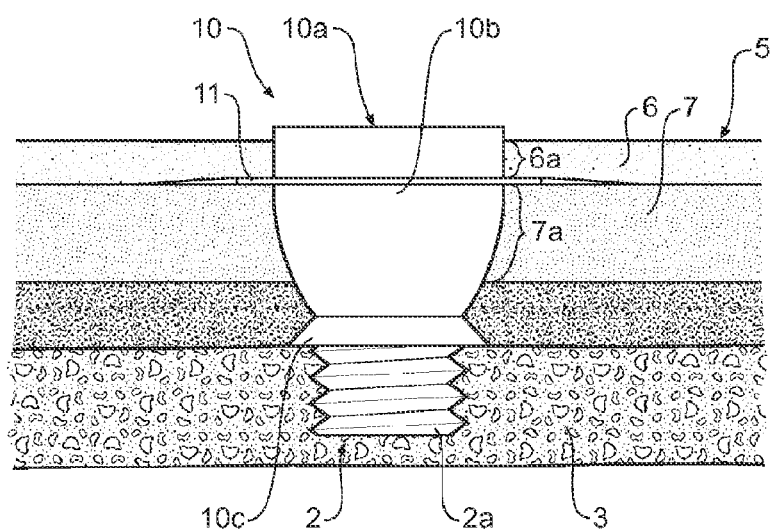
FIG. 2 illustrates a percutaneous bone-anchored implant in accordance with embodiments of the present invention.

FIG. 2 shows a bone-anchored implant 10 in accordance with embodiments of the present invention. As described with reference to FIG. 1, system 10 comprises abutment 10a having a main portion 10b, base 10c and fixture element 2 with screw thread 2a. It would be appreciated that fixture element 2 may take various forms and that the arrangement of FIG. 2 is merely illustrative. In certain embodiments, fixture element 2 may be as described in International Patent Application No. PCT/SE01/01506 (WO02/09622) entitled "Anchoring Element" and U.S. Pat. No. 4,498,461 entitled "Coupling to a Bone-Anchored Hearing Aid." The content of both of these documents is hereby incorporated by reference herein.

Implant 10 further comprises a barrier member 11. In this exemplary embodiment, barrier member is a ring positioned around abutment 10a. That is, barrier member 11 comprises a substantially planar member circumferentially extending from the surface of implant 10. Barrier member 10 has a thickness and a circumferential width between the surface of implant 10 and outer edge of the barrier member. When in position, barrier member 11 is located substantially between epidermis 6 and dermis 7. As such, barrier member 11 serves to separate epidermis 6 from the implant-dermis interface 7a, thereby reducing the phenomenon of epidermal down-growth described above. As used herein, the term "separate" will be understood by its meaning of "to keep apart" or "kept apart", and may encompass a temporary separation. It will also be appreciated that while reference is made to removing or separating a portion of the epidermis from the dermis, in a clinical setting, it is difficult to solely isolate the epidermis from the dermis, and in practice, a layer of epidermis removed or separated from the dermis may have retained a thin layer or portion of the dermis. It will thus be understood that when reference is made to separating or removing a portion of the epidermis from the debris, it will encompass situations where a portion of the dermis may be retained with the separated or removed epidermis.

As noted, barrier member 11 reduces the risk of epidermal down-growth, and allows dermis 7 to heal around implant system 10 without interference from the epidermis 6. Once dermis 7 has healed around and is sufficiently attached to implant 10 at implant-dermis interface 7a, barrier element 11 may be removed to allow epidermis 6 to reconnect to dermis 7 to complete the healing process around the implant.

As is well known, wound healing is a complicated process that generally consists of three sequential stages known as inflammation, proliferation and remodeling. In the inflammatory phase, bacteria and debris are phagocytosed and removed, and factors are released that cause the migration and division of cells involved in the proliferative phase. The proliferation stage is divided into three discreet processes: the formation of granulation tissue, epithelial migration and wound contracture. Granulation tissue forms in the base of healing wounds and has a red, glassy, granular appearance. The appearance of granulation tissue is largely due to the growth of new blood vessels, known as angiogenesis, and the formation of an extracellular matrix occurring after the wound has been sufficiently cleansed during the inflammatory stage. At the granulation stage, proteins of dermis 7 will attach to the surface of implant 10. At this point, dermis 7 is sufficiently attached to implant 10 so as to prevent epidermal down-growth. The granulation stage typically occurs 4-7 days after the opening of the wound.

Finally, in contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

Figure 3A:
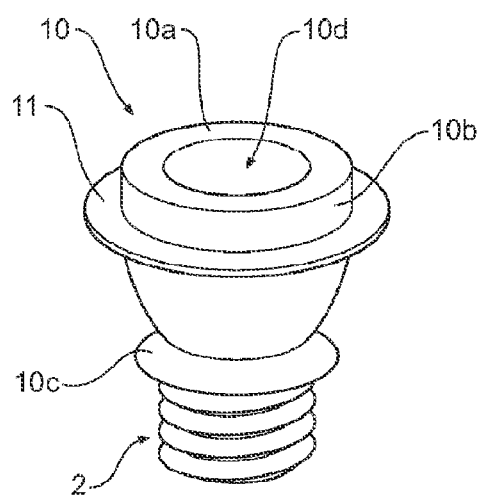
FIG. 3a is a perspective view of the bone-anchored implant of FIG. 2.
Figure 3B:
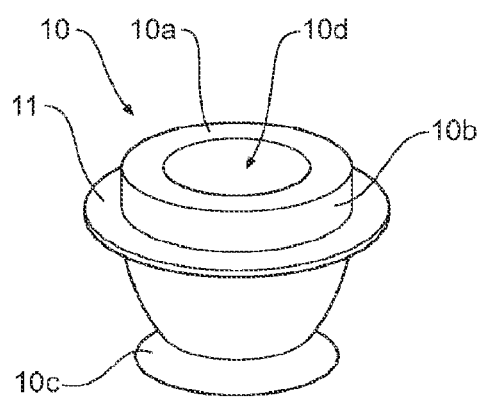
FIG. 3b is a perspective view of the abutment and barrier member of the bone-anchored implant of FIG. 2.

FIG. 3a is a perspective view of implant 10 of FIG. 2, while FIG. 3b is a perspective view of only abutment 10a of FIG. 2. As shown abutment 10a has an interior space 10d for receiving or interfacing with an external device such as a hearing aid device (not shown). As noted above, provided around implant 10 is barrier member 11, which in the example in FIG. 3a, is a ring surrounding implant system 10. In this example, barrier member 11 may be attached to implant 10 by, for example, temporary adhesive including, but not limited to, silicone adhesives or polyurethane adhesives. Alternatively, barrier member 11 may be removably attached to implant 10 via friction fit, snap fit or clipping arrangement. Specifically, in one embodiment, barrier member 11 further comprises a snap fit arrangement to snap-lock to the body. In another embodiment, barrier member 11 further comprises a clip arrangement configured to attach to the abutment. In a still other embodiment, barrier member 11 further comprises a magnet configured to magnetically to attach to the abutment.

In certain embodiments, barrier member 11 may be formed from a material that does not attach to surrounding tissue. For example, barrier member 11 may be a polymer including, but not limited to, polyurethane (degradable or non-degradable), polyetheretherketone (PEEK), silicone, polylactic acid, polyethylene (PE), collagen matrix (a bio-polymer), cellulose bio-polymer), or fibrous material. The barrier member 11 may, in some embodiments, be coated and/or impregnated with one or more anti-bacterial or anti-microbial substances such as (but not limited to) gentatnycin, penicillins, cephalosporins, rifampicin, vancomycin, quinolones, sulfonamides, and/or silver compounds. Barrier member 11 may also be coated and/or impregnated with anti-inflammatory substances such as glucocorticoides (e.g. dexamethasone), paracetamol and/or naproxen.

In embodiments of the present invention, the surface of the implant must be configured such that the dermis is able to firmly attach to the implant surface. Therefore, having an implant surface that provides a strong bond between the surface and the tissue is of great importance. One such surface is hydroxyl apatite, but several other ceramic surfaces and certain polymers may also be used. Additionally, structured surfaces, n the macro, micro or nano scale may also be used for improved adhesion.

For specifically, in certain embodiments of the present invention, the surface of implant 10 at one or more of the implant-epidermis interface 6a and the implant-dermis interface 7a is treated to facilitate integration. In one embodiment, the surface of implant 10 is coated with a biocompatible polymer or a ceramic material with a thickness of approximately 0.001 µm to approximately-50 µm. The coating is applied in such a way that non-interconnected pores or crevices are created. Generally the coating should be applied in such a way that a structured surface such as a porous surface or a surface with indentations or a fibrous surface is obtained. In such embodiments, the polymer coating is comparatively soft and decreases the shear stresses on the skin. In certain embodiments, a layer of a porous polymer is used for the coating with a thickness of about 30 nm. Such design is allowing skin 5 to heal into the polymer matrix. In other embodiments, a polymer containing a pharmaceutical drug that increases the production of extra-cellular matrix proteins in the soft tissue, such as collagen or keratin, might be used. The increased stability of the tissue increases the resistance to shear stress.

Other types of materials might be used for increasing the skin tissue integration. Specifically, chemical substances such as pharmaceutical drugs and antioxidants, or biochemical substances such as proteins, biopolymers, growth factors, DNA, RNA or biominerals might be used. These substances are then associated to the implant with a purpose of increasing the amount of, or number of connections to extra cellular matrix proteins. Antibiotic, steroid or anti-inflammatory substances might also be used.

An alternative surface treatment to coatings or substances, or in combination, a surface enlargement treatment can be provided to the surface of the skin contacting part of the percutaneous implant in order to increase the surface roughness. Such treatment can be achieved by using techniques that includes grit-blasting, polishing, micro-machining, laser treatment, turning, anodic oxidation, oxidation, chemical etching, sintering or plasma deposition of a titanium surface. Preferably such treatment should result in a 10% surface increase, compared to a conventional machined surface and a roughness value Sa of approximately 0.5 µm to approximately-10 µm, measured by means of White Light Interferometry.

In particular embodiments, the treatment is only at implant-dermis interface 7a to facilitate attachment between dermis 7 and implant 10.

Further details of surface treatments are described in commonly owned and co-pending U.S. patent application Ser. No. 12/601,801, filed on Nov. 24, 2009. The content of this application is hereby incorporated by reference herein.

Returning to barrier member 11, as noted above the member is positioned so as to separate epidermis 6 from dermis 7. In some embodiments, the distance between the top of the abutment 10a and the barrier member 11 may be approximately 1 mm to approximately 5 mm. The distance from the side of abutment 10a and the end of barrier member 11 may be approximately 1 mm to approximately 20 mm. The thickness of barrier member may be approximately 0.5 mm to approximately 1 mm. It would be appreciated that the ranges of values provided above are merely exemplary, and different ranges may be used. The actual values of these dimensions may be determined depending upon the type of materials used, as would be understood by the person skilled in the art.

The distance between the top of abutment 10a and barrier member 11 may vary depending on a number of factors, such as the thickness of epidermis 6. These factors may be considered in selecting the above distances. In specific embodiments, the location of barrier member 11 is adjustable along abutment 10a to account for varying thickness. This adjustment may be provided through one of the removable attachment mechanisms described above.

In embodiments of the present invention, barrier member 11 may be provided by a degradable material that dissolves over time. In specific such embodiments, the barrier member 11 is dissolved at approximately the same time as the dermis 7 has fully attached to the implant at the implant/dermis interface 7a (e.g. at the granulation stage). Accordingly, epidermis 6 is then allowed to fully cover the dermis and attach to implant 10 at implant-epidermis interface 6a. Examples of suitable dissolvable materials include synthetic polymer groups such as polylactic acid, polycaprolactone, polyanhydrides, polyglycolic acid; and degradable bio-polymers such as Collagen. Suitable degradable materials may include biodegradable materials.

Embodiments of the present invention have been described above with reference to barrier member 11 being attached to implant 10. In certain embodiments, barrier member 11 is not in contact with implant, but is rather may be placed separately around the implant between the dermis 7 and the epidermis 6. In such embodiments, the distance between barrier member 11 and implant 10 is selected to as to impede epidermal down-growth at the implant/dermis interface 7a.

Figure 4A:
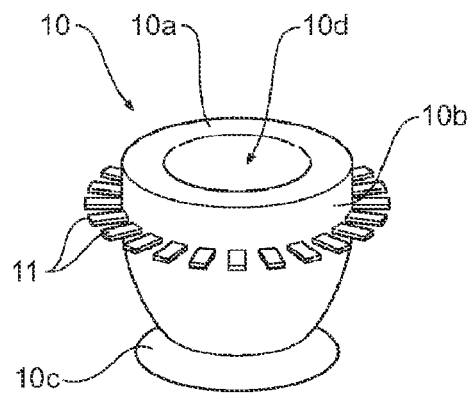
FIG. 4a is a perspective view of the abutment of FIG. 2 and an alternative barrier member.

FIG. 4a illustrates another alternative of the barrier member 11 around implant 10. As shown, in this embodiment, barrier member 11 consists of a plurality of individual sub-elements extending from the surface of implant 10. In such embodiments, the distance between the sub-elements and/or the thickness of the elements is selected so as to impede epidermal down-growth for a time period that is sufficient to allow attachment of dermis 7 to implant 10.

Figure 4B:
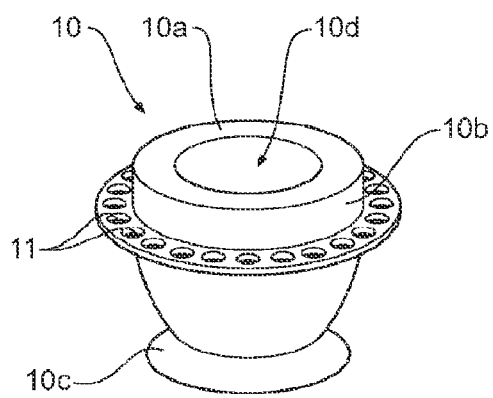
FIG. 4b is a perspective view of the abutment of FIG. 2 and an alternative barrier member.

In a further alternative, as shown in FIG. 4B, barrier member 11 may be provided by a continuous ring with apertures. In such embodiments, the distance between the apertures and/or size of the apertures is selected so as to impede epidermal down-growth for a time period that is sufficient to allow attachment of dermis 7 to implant 10.

Figure 5:
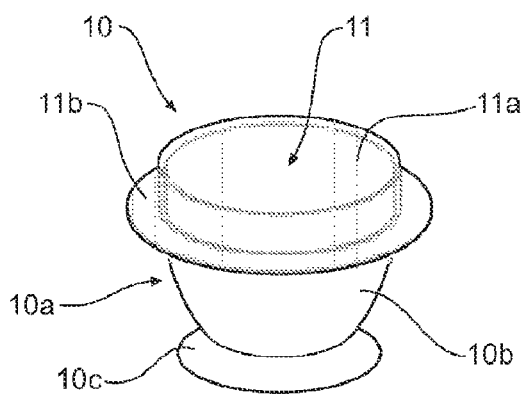
FIG. 5 is a perspective view of the bone-anchored implant of FIG. 2 and a still other alternative barrier member.
Figure 5A:
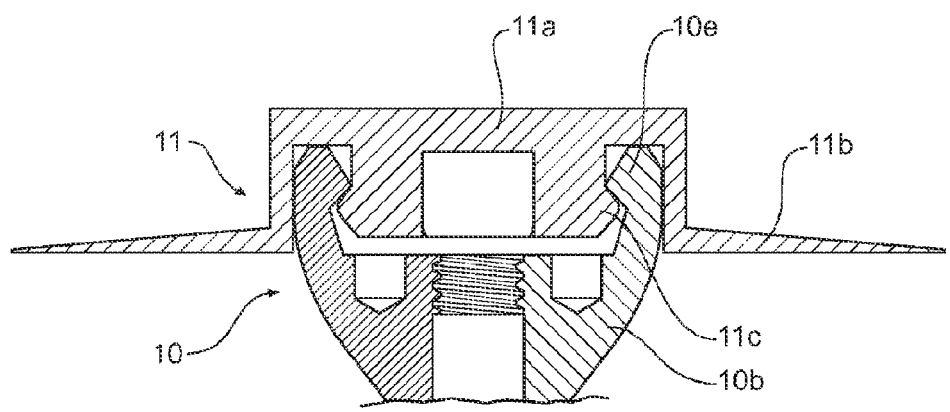
FIG. 5A is a cross-sectional of the barrier member of FIG. 5 shown positioned over the abutment.

Another embodiment of the present invention is shown in FIGS. 5 and 5a. In these embodiments, barrier member 11 is provided as an annular flange 11b protruding from around a cap 11a. As shown, cap 11a may be placed over the abutment 10a of implant 10.

In the embodiments of FIGS. 5 and 5a, barrier member 11 may be attached to abutment 10a via, for example, snap-fit, or friction fit. Alternatively, barrier member 11 may be clipped or screwed on abutment 10a and is referred to herein as a clip-on or screw-on barrier member 11, respectively.

FIG. 5a is a cross-sectional view illustrating one exemplary embodiment in which barrier member 11 is attached to abutment 10a over main portion 10b with a 'snap portion' 11c. More specifically, to retain barrier member 11 to abutment 10a, cap 11a is placed over interior space 10d such that an annular protrusion 13 extends into interior space 10d of abutment 10a. When protrusions 13 are forced into interior space 10d, snap portion 11c deflected by interior lip 10e and resiliently return to their original state into place under lip 10e, thereby retaining barrier member 11 to abutment 10a. Barrier member 11 may be later detached from abutment 10a by the application of a sufficient upward force to deflect the protrusions of snap portion 11c inwards and over the interior tip 10c to release barrier member 11.

An example of a suitable material for the barrier member of FIGS. 5 and 5A is PEEK.

Figure 6:
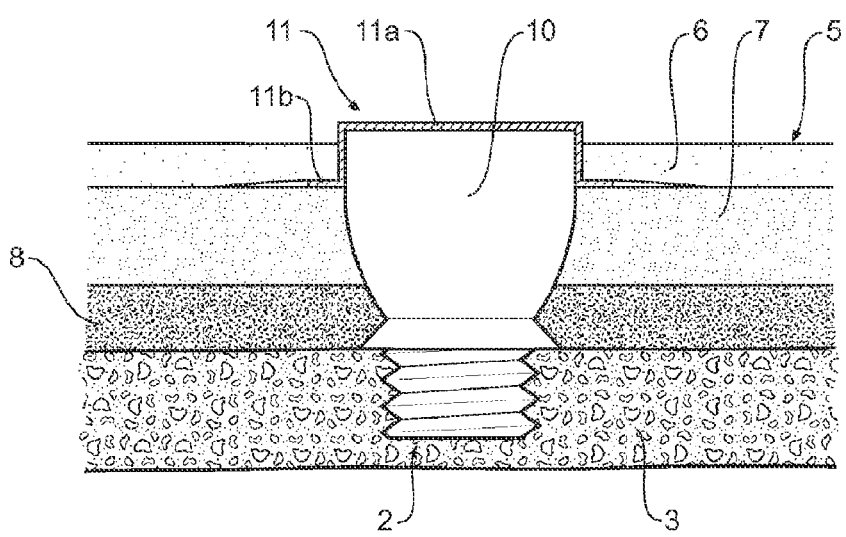
FIG. 6 illustrates the bone-anchored implant of FIG. 5 implanted in a recipient.

FIG. 6 illustrated implant 10 and barrier member 11 of FIG. 5, implanted in the recipient. As may be seen, annular flange 11b is located between epidermis 6 and dermis 7, thus preventing epidermal down-growth into the implant-dermis interface 7a. When dermis 7 has fully attached to implant 10 at the implant-dermis interface 7a, barrier member 11 may be removed, thereby allowing epidermis 6 to grow over dermis 7 around implant 10 and form its own attachment to the implant.

Figure 7:
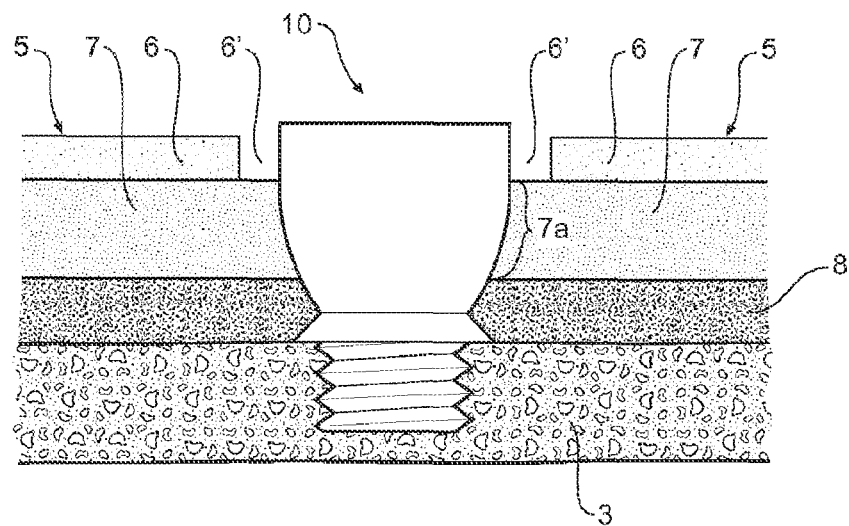
FIG. 7 illustrates a bone-anchored implant implanted in accordance with one exemplary method of the recipient of the present invention.

Embodiments of the present invention described above are generally directed to separating epidermis 6 and dermis 7 through the use of a physical barrier member 11. As previously noted, in other embodiments epidermis 6 may be separated from dermis 7 by a barrier formed via a surgical procedure in which a portion of the epidermis around implant 10 is removed. An exemplary such arrangement is shown in FIG. 7 in which a annular shaped portion of epidermis 6 is removed around the outer surface of implant 10. This arrangement allows dermis 7 time to heal and attach to implant 10 at the implant-dermis interface 7a before epidermis 6 grows back over the dermis 7 to meet implant 10. This again reduces the likelihood of epidermis down-growth at the implant system/deaths interface 7a because, by the time epidermis 6 reaches implant 10, dermis 7 is sufficiently attached to the implant.

Figure 8:
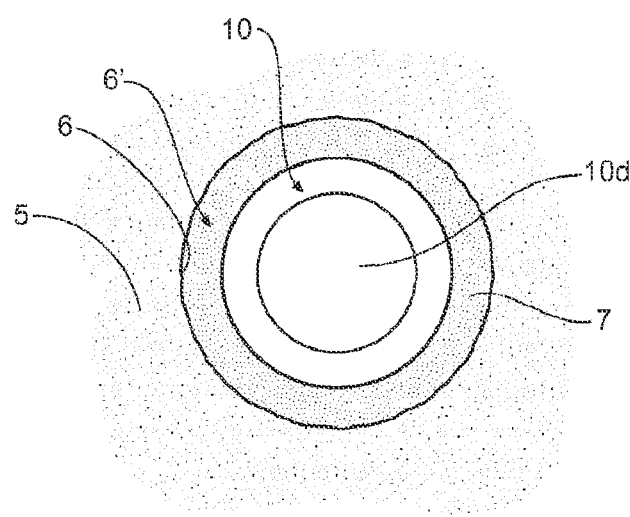
FIG. 8 is a top view of the arrangement of FIG. 7.

FIG. 8 is a top view of the arrangement of FIG. 7 in which implant 10 is implanted in the recipient. As shown, implant 10 has a open interior space 10d of the abutment 10a. Surrounding implant 10 is dermis 7, which is left uncovered by epidermis 6 through removal of a portion of epidermis 6. Accordingly, a space 6' is between the surface of implant 10 and the edge of epidermis 6.

In one example, space 6' left by removing a portion of epidermis 6 may be anywhere from about 0.1 mm to about 10 mm. However, it would be appreciated that any suitable amount of epidermis 6 may be removed to allow sufficient time for the dermis 7 to satisfactorily attach to implant 10 at implant-dermis interface 7a before the healing epidermis 6 reaches the implant. For example, if it is estimated that dermis 7 will take approximately 4 to 7 days to satisfactorily attach to implant 10. It is estimated that epidermis 6 will grow over dermis 7 at a rate of about 0.25 mm to about 0.5 mm per day. Accordingly, the amount of epidermis 6 removed may be about 2 mm to about 5 mm from abutment 10a. A wound dressing and/or antibacterial substances could be applied to the open wound of the exposed dermis 7 in area 6'.

As noted above, attachment of dermis 7 to implant 10 may take approximately 4-7 days. However, various factors may influence the rate of healing and attachment of dermis 7 to implant 10, In certain embodiments, attachment may be affected by the provision of an enhanced healing surface either by modification of the surface, as described in International Patent Application No. PCT/SE2008/000337 entitled "Implant Abutment" or by the provision of healing-enhancing substances at the implant/dermis interface 7a, such as amelogenin, platelet derived growth factor (PDGF), and/or fibroblast growth factor (FGF). In such a case where the healing and attachment time of the dermis is expected to be reduced by the provision of such an environment, the amount of epidermis 6 removed about implant 10 may be reduced.

Alternatively, substances may be applied to epidermis 6 to retard the growth of epidermis 6 towards the implant/dermis interface 7a, thereby allowing less of the epidermis to be removed. One exemplary substance that may retard the growth of epidermis 6 is a medication known as Acitretin that is sold under the trade name Soriatane®.

Figure 9:
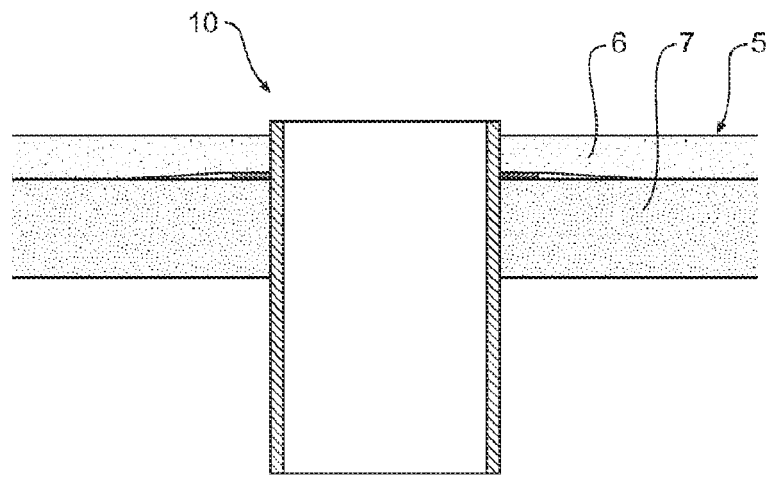
FIG. 9 is a cross-sectional view of an alternative percutaneous implant m accordance with embodiments of the present invention.

Embodiments of the present invention have been primarily described above with reference to percutaneous implants in the form of bone-anchored implants usable with bone conduction hearing aid devices. However, as previously noted, various aspects of the present invention may be used in relation to any bone-anchored or non-bone-anchored percutaneous implant, including catheters, tracheotomy devices, and orthopaedic external fixation devices. FIG. 9 shows the use of a percutaneous implant in a non-bone anchored application. In arrangement of FIG. 9, implant 10 i is a hollow cylinder implanted through skin 5 to allow internal access to the body through the skin. As shown, in these embodiments implant 10 includes a barrier member 11 which when implanted, epidermis 6 and dermis 7 are separated by barrier member 11 to thereby inhibit epidermal down-growth as previously described.

Figure 10:
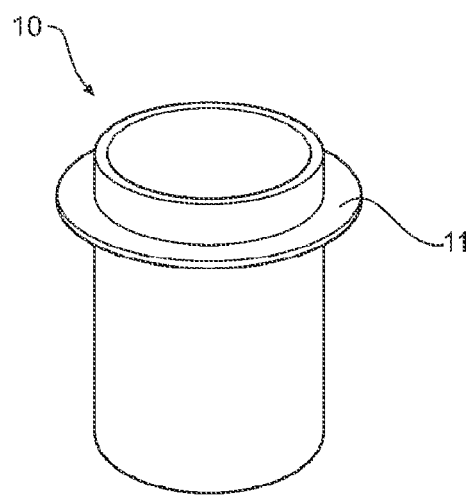
FIG. 10 is a perspective view of the percutaneous implant of FIG. 9.

FIG. 10 shows a perspective view of a generic percutaneous implant system 10 with barrier member 11 as shown in FIG. 9.

Embodiments of the present invention also include methods for reducing a risk of infection around an implanted percutaneous implant through skin of a recipient by separating the epidermis from the dermis at the implant-dermis interface. In one aspect of the present invention, this may be accomplished by providing a barrier between the epidermis and the dermis at the implant system. In another aspect, this may be accomplished by removing at least a portion of the epidermis from the dermis around the implant system.

Figure 11A:
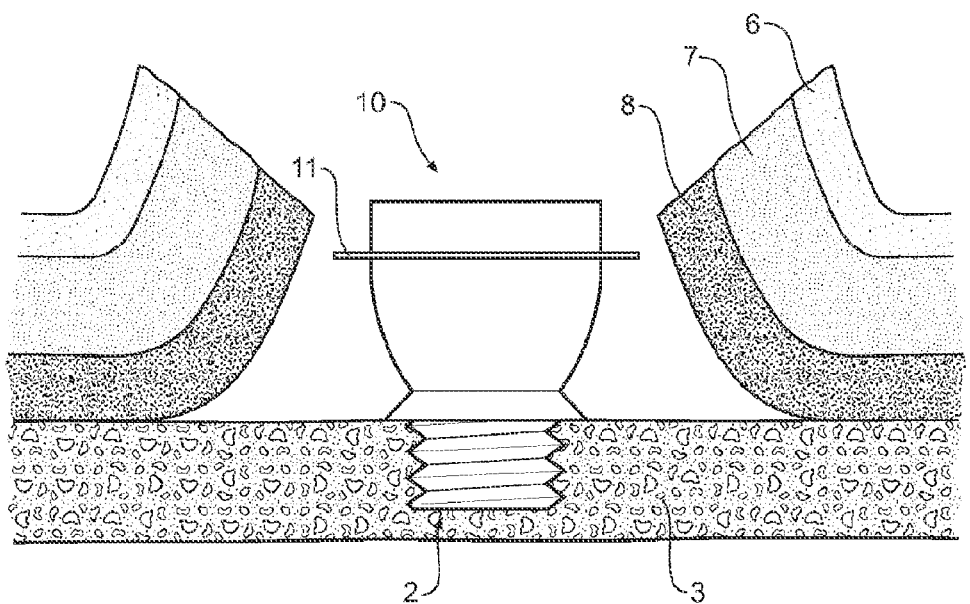
FIG. 11A illustrates a first step in implanting a bone-anchored implant according to one aspect of the present invention.
Figure 11B:
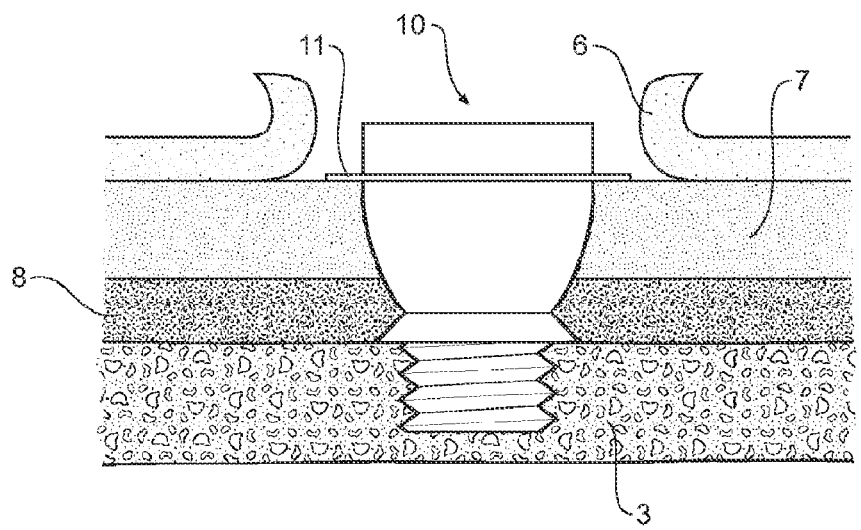
FIG. 11B illustrates a second step in implanting a bone-anchored implant according to one aspect of the present invention.
Figure 11C:
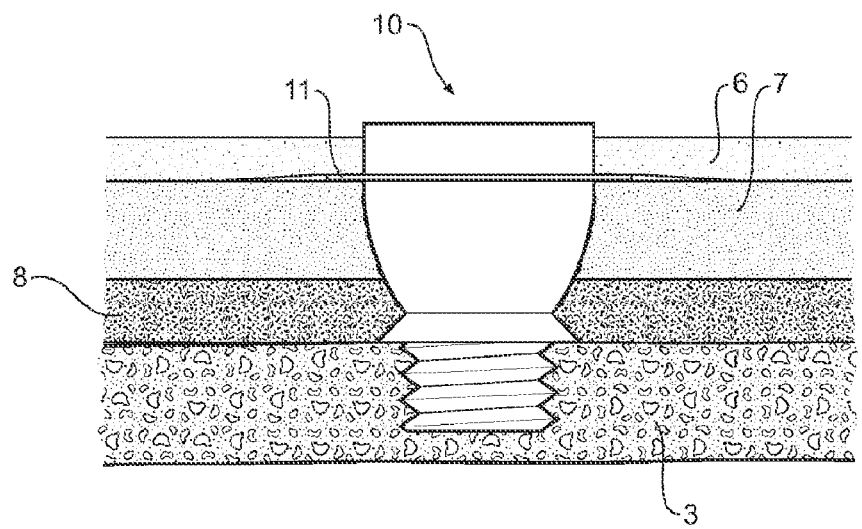
FIG. 11C illustrates a third step in implanting a bone-anchored implant according to one aspect of the present invention.
Figure 11D:
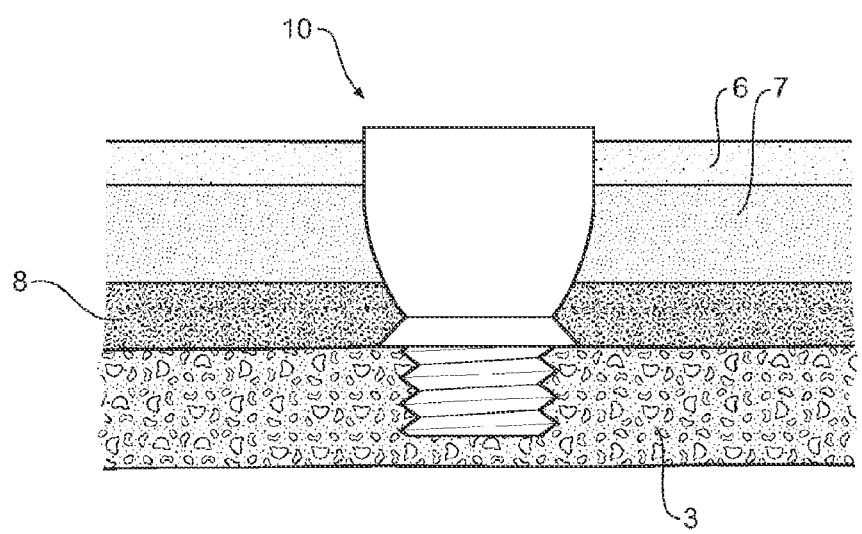
FIG. 11D illustrates shows a fourth step in implanting a bone-anchored implant according to one aspect of the present invention.
Figure 12:
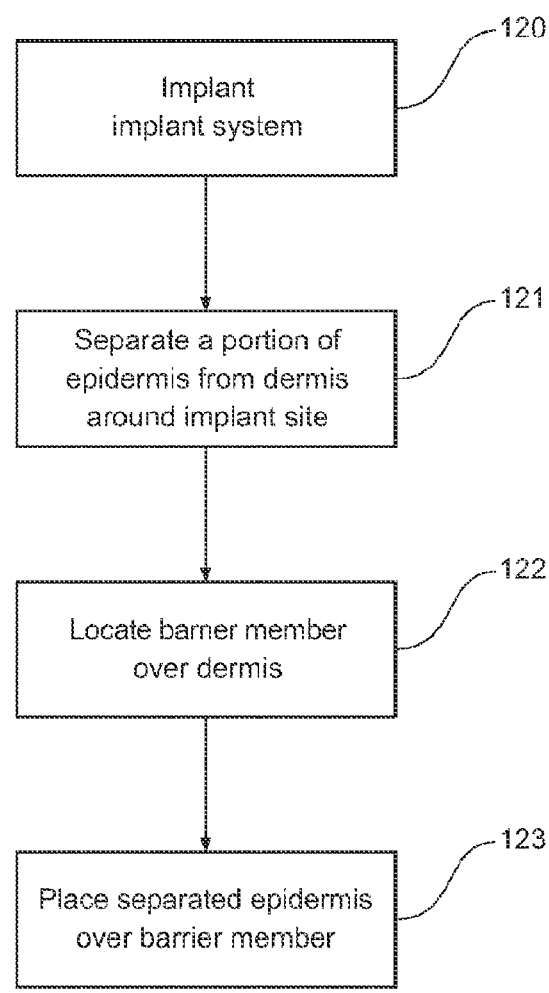
FIG. 12 is a flowchart of the method shown in FIGS. 11A to 11D.

FIG. 12 is a flowchart illustrating the implantation of an implant 10 and barrier member 11 in accordance with a method of the present invention. Each step of the method of FIG. 12 is illustrated in FIGS. 11A-11D.

The method of FIG. 12 begins at step 120, the implant is positioned in the recipient. In the case of a bone-anchored implant, this may involve anchoring the implant system to the bone via, for example, a screw. In the case of a non-bone-anchored implant system, it will not be necessary to anchor the implant system to bone. An exemplary positioning according to step 120 is shown in FIG. 11A. As shown, bone 3 at the implant site is exposed by performing an incision and pulling back the tissue over the bone, including skin 5 with epidermis 6, dermis 7 and other tissue 8. Implant 10 is then secured to the bone 3 by any suitable means, such as via fixture element 2. If the implant system is not a bone anchored implant, then the step of securing the implant to the hone would be omitted.

Returning to FIG. 12, at step 121, a portion of epidermis 6 is separated from the underlying dermis 7 around implant 10. FIG. 11B illustrates a portion of epidermis 6 around implant 10 after it has been pulled away from dermis 7, and after the dermis and other tissue 8 have been pushed back onto the bone 3 around implant 10. As shown, dermis 7 is pushed under barrier member 11.

At step 122, the barrier member is located on top of the dermis and at step 123, the separated portion of the epidermis is placed over the barrier member. In FIG. 11C, epidermis 6 is placed over dermis 7 and over barrier member 11. As shown, barrier member 11 separates dermis 7 from epidermis 6 at the implant-dermis interface 7a.

Additionally, FIG. 11D shows the implant after some time, when the dermis 7 andother tissue 8 have satisfactorily healed and attached to the implant 10. As shown, barrier member 11 has been removed to allow epidermis 6 to attach to dermis 7 around implant 10. As previously noted, in certain embodiments, barrier member 11 does not adhere to either of epidermis 6 or dermis 7. As such, after dermis 7 is sufficiently attached to implant 10, the flaps of epidermis may be opened and barrier member 11 may be simply removed. In other embodiments noted above, barrier member is resorbable and does not need to be removed.

It will be appreciated that certain steps of the method of FIG. 12 may be performed in a different order, for example, the step of separating the epidermis from the dermis may be done prior to implanting the implant system.

It will also be appreciated that in some examples, barrier member 11 may not even be attached or otherwise associated with implant 10, and may simply be provided as a separate member or ring which is placed over the dermis layer. In such embodiments, barrier member 11 is placed around implant 10 and then epidermis 6 is placed on top of the barrier member. In this example, the separate barrier member may comprise an integral piece or two or more separate pieces which together, form a sufficient barrier to inhibit epidermal down-growth and thus reduce the likelihood of infection about the implant site.

Figure 13A:
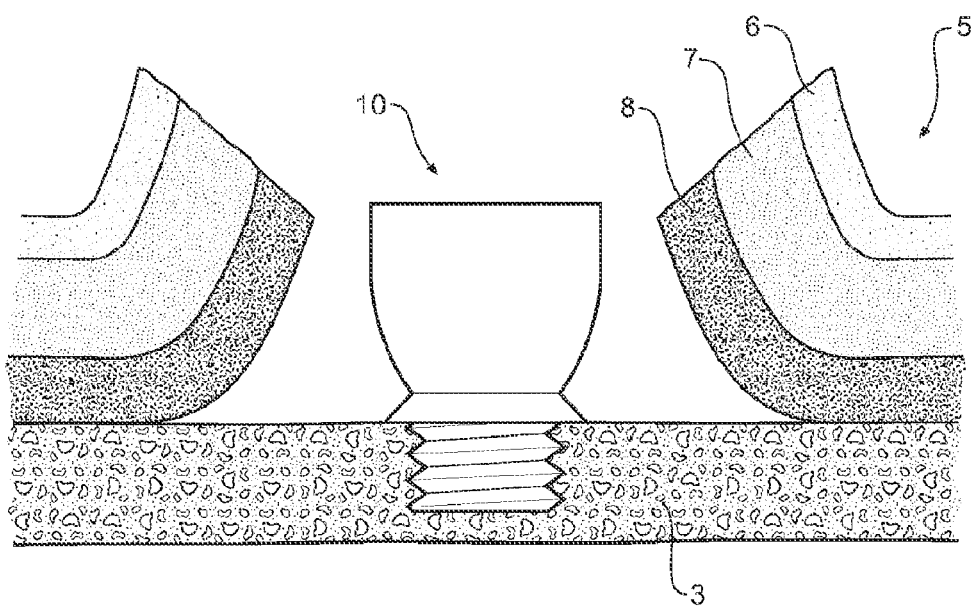
FIG. 13A illustrates a first step in implanting a bone-anchored implant according to another aspect of the present invention.
Figure 13B:
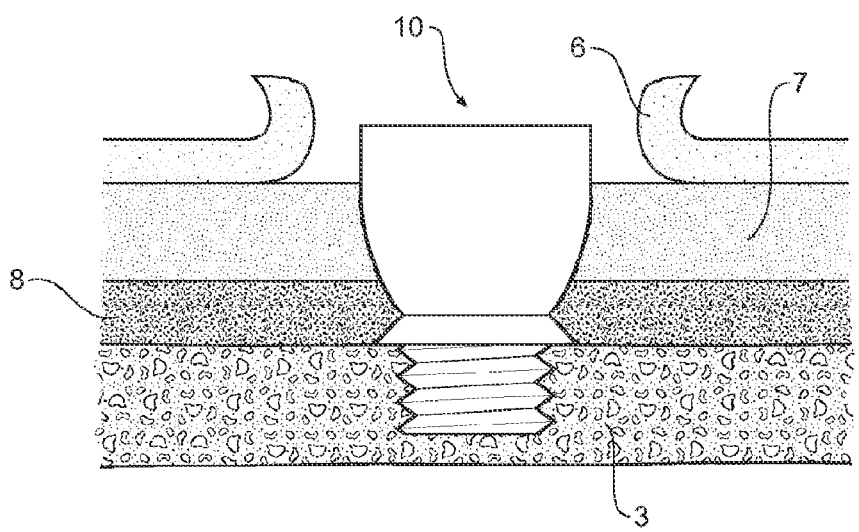
FIG. 13B illustrates a second step in implanting a bone-anchored implant according to another aspect of the present invention.
Figure 13C:
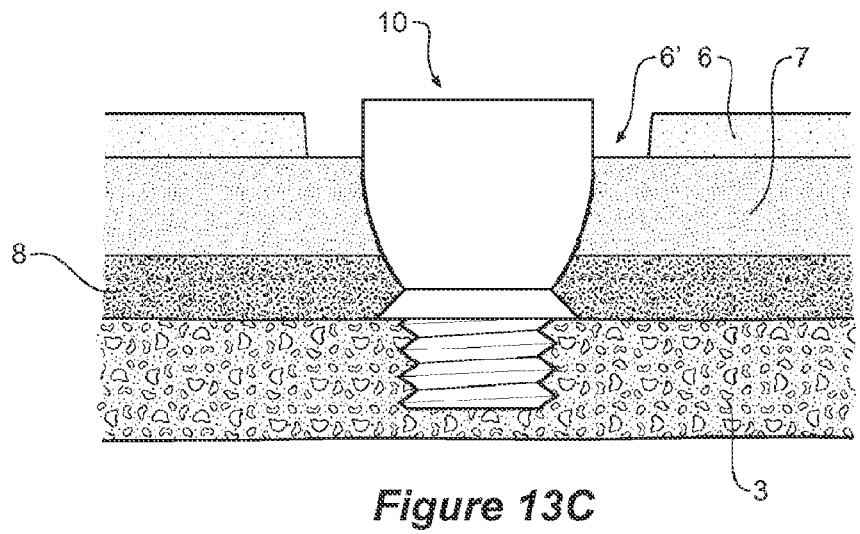
FIG. 13C illustrates a third step in implanting a bone-anchored implant according to another aspect of the present invention.
Figure 13D:
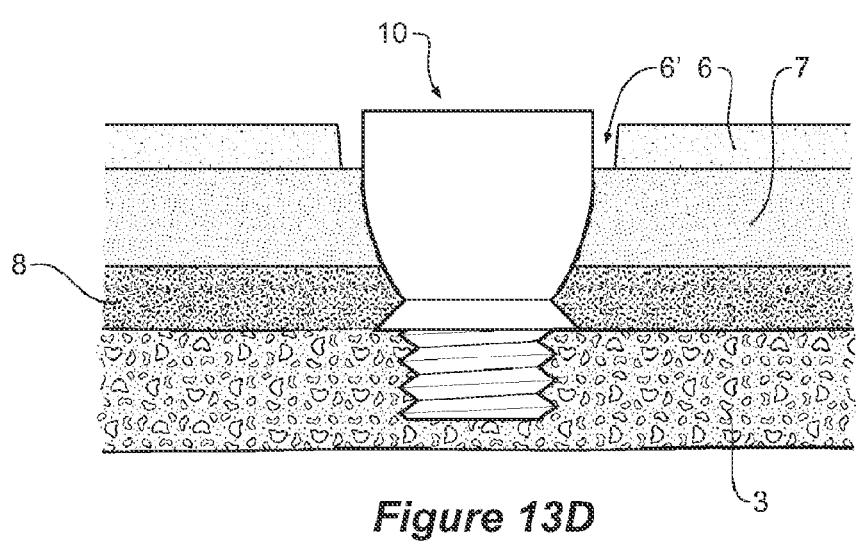
FIG. 13D illustrates shows a fourth step in implanting a bone-anchored implant according to another aspect of the present invention.
Figure 14:
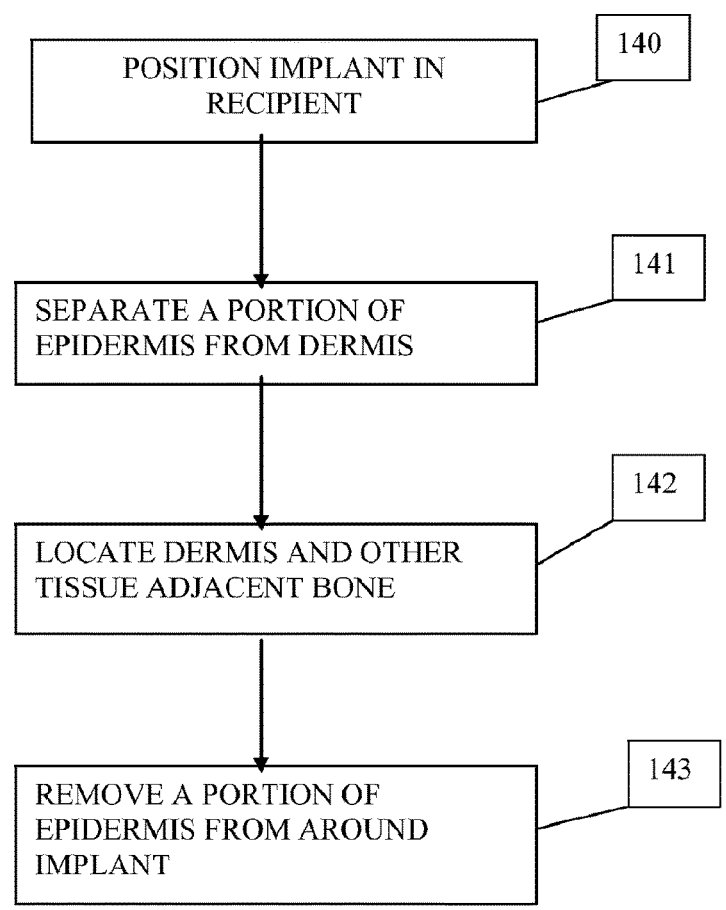
FIG. 14 is a flowchart of the method shown in FIGS. 13A to 13E.

FIG. 14 is a flowchart illustrating the implantation of an implant 10 a in accordance with a method of the present invention in which a portion of tile epidermis is removed as described above, and in which the use of a barrier member may not be required. Each step of the method of FIG. 12 is illustrated in FIGS. 13A-13D.

The method of FIG. 14 begins at step 140 where implant 10 is positioned in the recipient. In the case of a bone-anchored implant, this may involve anchoring the implant system to the bone via, for example, a screw. In the case of a non-bone-anchored implant system, it will not be necessary to anchor the implant system to bone. An exemplary positioning according to step 140 is shown in FIG. 13A. As shown, bone 3 at the implant site is exposed by performing an incision and pulling back the tissue over the bone, including skin 5 with epidermis 6, dermis 7 and other tissue 8. Implant 10 is then secured to the bone 3 by any suitable means, such as via fixture element 2. If the implant system is not a bone anchored implant, then the step of securing the implant to the bone would be omitted.

Returning to FIG. 14, at step 141, a portion of epidermis 6 is separated from the underlying dermis 7 around implant 10. FIG. 13B illustrates a portion of epidermis 6 around implant 10 after it has been pulled away from dermis 7, and after the dermis and other tissue 8 have been pushed back onto the bone 3 around implant 10 in accordance with step 142 of FIG. 14.

In step 143 of FIG. 14, a portion of the epidermis 5 around the implant is removed, to provide a space 6' between the implant 10 and the implant system/dermis interface 7a, thereby separating the epidermis 5 from the implant system/dermis interface 7a. This is shown in FIG. 13C.

FIG. 13D shows the arrangement in FIG. 13C after some time has elapsed, and dermis 7 and other tissue 8 have been allowed to heal and attach to implant 10. In this way, because epidermis 6 was separated from implant-dermis interface 7a for a period of time, the appropriate healing and attachment of dermis 7 to implant 10 has been allowed to occur.

Figure 13E:
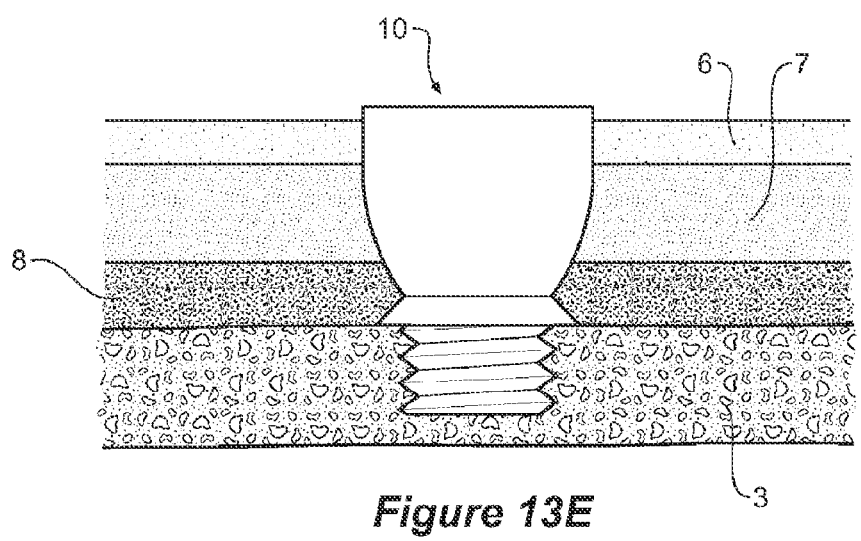
FIG. 13E illustrates shows a fifth step in implanting a bone-anchored implant according to another aspect of the present invention.

As shown in FIG. 13E, by the time that epidermis 6 has reached the implant 10, there is no gap between implant 10 and dermis 7 at implant-dermis interface 7a. Accordingly, there is no area for epidermis down-growth to occur, and therefore no interference with the attachment of dermis 7 to implant 10. This then reduces the risk of infection around the implant as previously described.

Another exemplary implant procedure is shown with reference to FIGS. 15A to 15E. In this example, an underlying portion of the dermis is shown to have been retained with the removed or separated layer of epidermis, as is likely to occur in practice. Specifically, as previously described, in all of the above examples, in some cases, a portion of underlying dermis may be retained with the portion of the removed or separated epidermis.

Figure 15A:
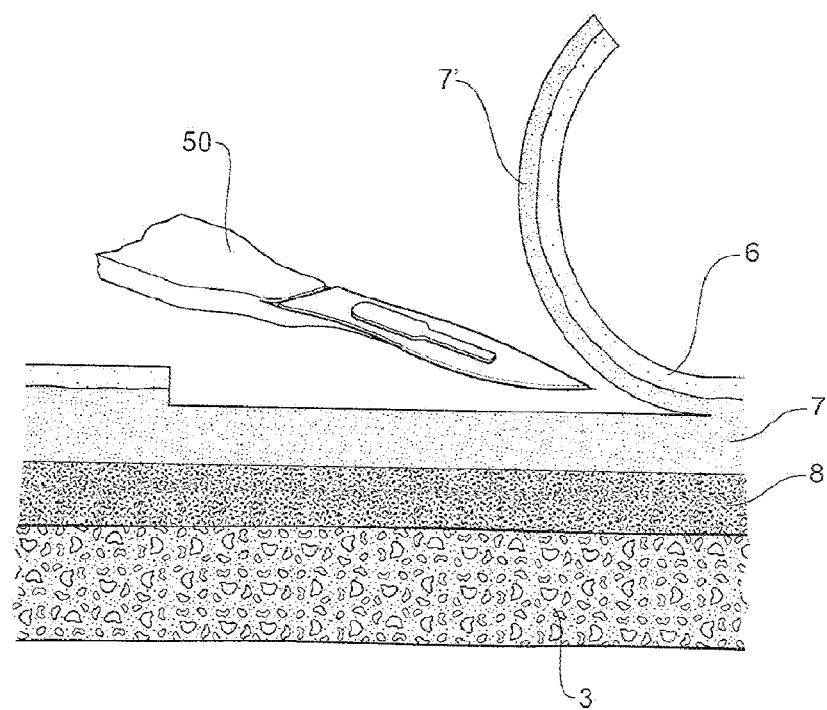
FIG. 15A illustrates a first step in another method of implanting a percutaneous implant system according to a still other aspect of the present invention.
Figure 15B:
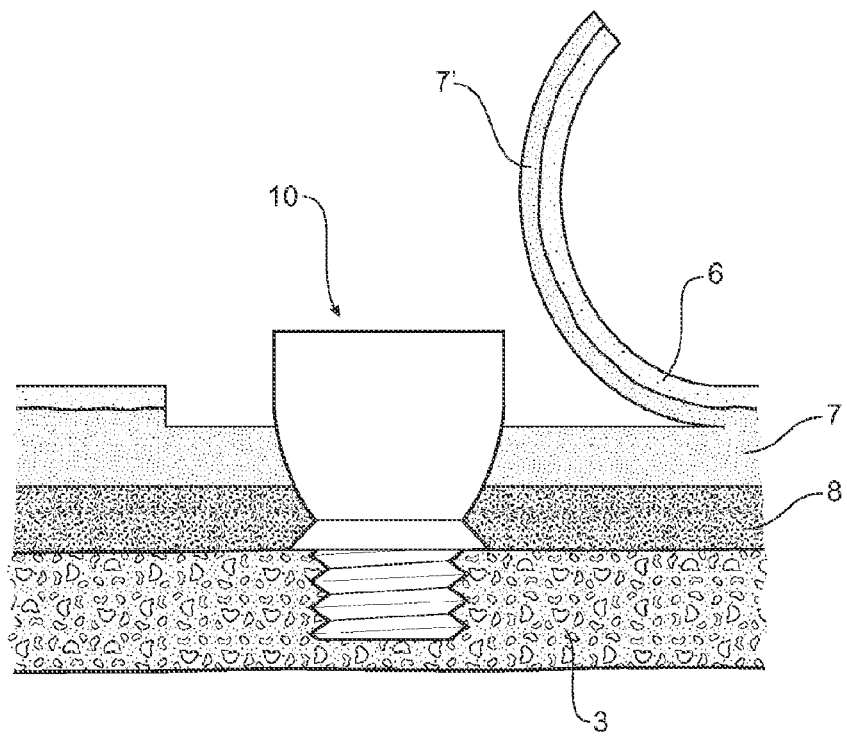
FIG. 15B illustrates a second step of another method of implanting a bone-anchored implant according to a still other aspect of the present invention.
Figure 15C:
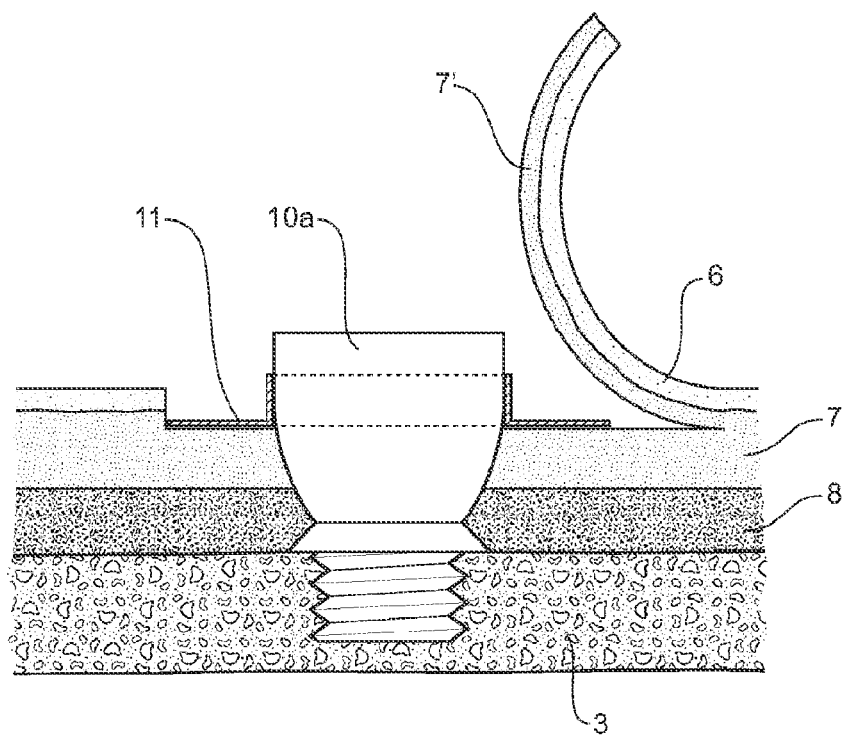
FIG. 15C illustrates shows a third step of another method of implanting a bone-anchored implant according to a still other aspect of the present invention.

In FIG. 15A, a thin skin flap is created using a scalpel 50 or a dermatome. The flap consists of mainly epidermis 6 (and as mentioned earlier, some dermis 7' as well). In FIG. 15B, implant 10 is shown implanted into the bone 3 of the recipient, and in FIG. 15C, there is shown barrier member 11 located over abutment 10a in turtle neck fashion by being pushed over abutment 10a and into place over dermis 7.

Figure 15D:
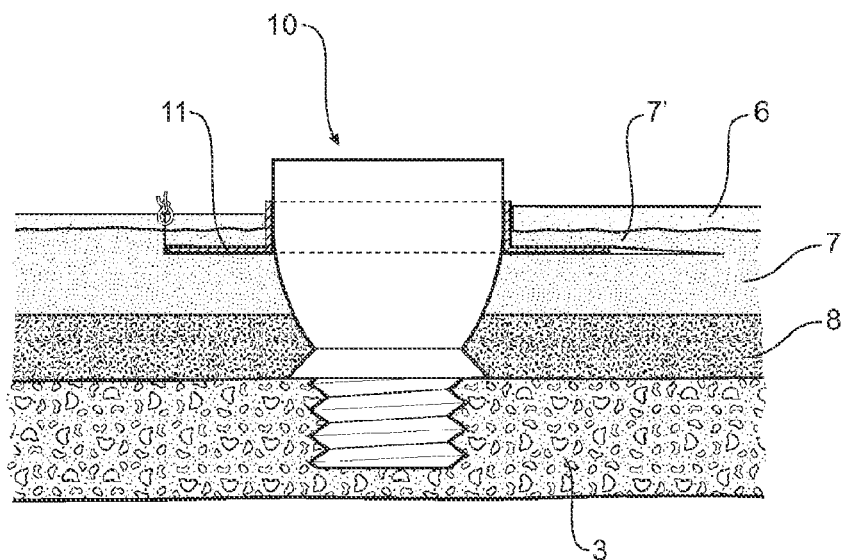
FIG. 15D illustrates shows a fourth step of another method of implanting a bone-anchored implant according to a still other aspect of the present invention.
Figure 15E:
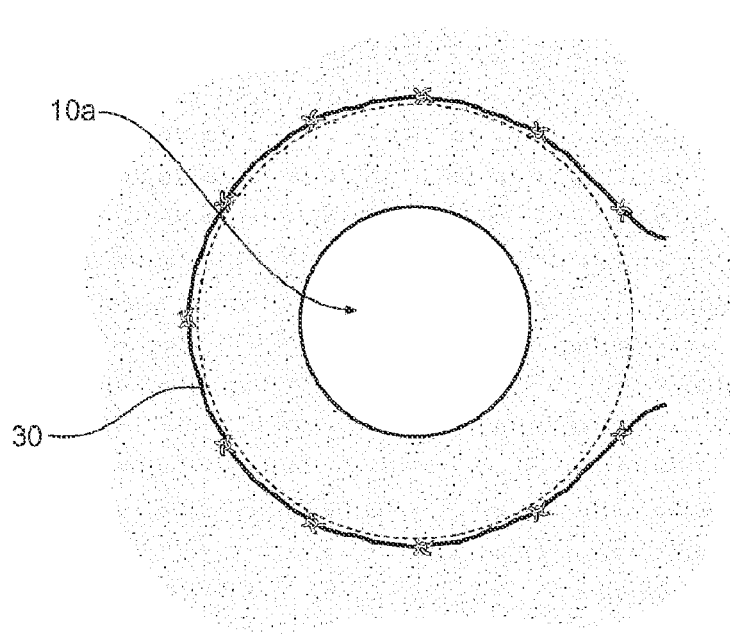
FIG. 15E illustrates shows a final step of another method of implanting a bone-anchored implant according to a still other aspect of the present invention.

FIG. 15D (a top view) illustrates that the flap comprising epidermis 6 and the portion of dermis 7' is placed on top of abutment 10a and a hole is cut or punched out of the flap and the abutment is pressed through. The flap is then sutured down, as indicated by suture line 30.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All documents, patents, journal articles and other materials cited in the present application are hereby incorporated by reference.

What is claimed is:

1. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted, wherein the barrier member is configured to obtain total separation of the epidermis from the dermis at locations of the barrier member.

2. The apparatus of claim 1, wherein the barrier member is removable from the body portion.

3. The implant of claim 1, wherein the barrier member is removable from the body portion such that the epidermis can come into direct contact with the dermis at locations where such contact was previously prevented by the barrier member.

4. The implant of claim 1, wherein the barrier member also completely covers an end of the body portion.

5. The implant of claim 1, further comprising a facial prosthesis attached to the body portion.

6. The implant of claim 1, wherein the percutaneous implant is part of an orthopedic fixation device.

7. The implant of claim 1, wherein the percutaneous implant is part of a device that is different from a bone conduction device.

8. The apparatus of claim 1, wherein the barrier member is configured to prevent epidermal down-growth.

9. The implant of claim 1, wherein the barrier member includes skin interfacing surfaces, which surfaces are smooth.

10. The apparatus of claim 1, wherein the barrier member is configured to resist attachment to tissue of the recipient thereto.

11. The implant of claim 1, wherein the percutaneous implant is part of a non-bone anchored implant system.

12. The implant of claim 1, wherein the barrier member is a temporary barrier.

13. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted,
wherein the barrier member is configured to resist skin attachment at a dermis facing side and an epidermis facing side.

14. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted,
wherein the percutaneous implant is part of a non-bone anchored implant system.

15. The apparatus of claim 14, wherein the barrier member is configured to prevent epidermal down-growth.

16. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted,
wherein the barrier member includes portions extending outward from the body portion that have a solid cross-section.

17. The implant of claim 16, wherein the barrier member comprises:
a cap configured to extend over the top of the body portion.

18. The implant of claim 16, further comprising a facial prosthesis attached to the body portion.

19. The apparatus of claim 16, wherein the portions extending outward from the body portion that have a solid cross-section separate the epidermis from the dermis.

20. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted,
wherein the barrier member is a temporary barrier.

21. The implant of claim 20, wherein the barrier member includes skin interfacing surfaces, which surfaces are smooth.

22. The apparatus of claim 20, wherein the barrier member is configured to resist attachment to tissue of the recipient thereto.

23. The implant of claim 20, wherein the barrier member comprises:
a cap configured to extend over the top of the body portion.

24. A percutaneous implant comprising:
a body portion configured to extend through the skin of a recipient, the skin having an epidermis and a dermis, the body portion including a surface with an epidermis facing portion positioned to be on a same level with respect to a longitudinal axis of the body portion as the epidermis and a dermis interface positioned to contact the dermis when the percutaneous implant is implanted in the recipient; and
a barrier member positioned around the body portion between the epidermis facing portion and the dermis interface to substantially separate the dermis from the epidermis at the surface of the body portion of the implant when the percutaneous implant is implanted, wherein
the epidermis facing portion is an epidermis interface positioned to contact the epidermis and is free of contact with the barrier member.

25. The apparatus of claim 24, wherein the barrier member is configured to resist attachment to tissue of the recipient thereto.

26. The implant of claim 24, wherein the barrier member includes skin interfacing surfaces, which surfaces are smooth.

27. The implant of claim 24, wherein the barrier member is configured to obtain total separation of the epidermis from the dermis at locations of the barrier member.

28. The implant of claim 27, wherein the barrier member is configured to permit the dermis to attach to the body member via growth to an outer surface of the body member, and wherein the barrier member is configured to prevent contact of the epidermis with the body member everywhere.

29. The implant of claim 27, wherein the barrier member is configured to permit the dermis to attach to the body portion via growth to an outer surface of the body portion, and wherein the barrier member is configured to prevent epidermal down-growth between the dermis and the body portion.

30. The implant of claim 24, wherein the barrier member is configured to permit the dermis to attach to the body portion via growth to an outer surface of the body portion, and wherein the barrier member is configured to prevent contact of the epidermis with the body portion due to growth of the epidermis while the barrier member is in place.

31. The implant of claim 24, wherein the barrier member includes skin interfacing surfaces, which surfaces are smooth.

32. The implant of claim 24, wherein the percutaneous implant is part of an orthopedic fixation device.

33. The apparatus of claim 24, wherein the barrier member is configured to prevent epidermal down-growth.

* * * * *